US012558518B2

(12) United States Patent
Niederhauser et al.

(10) Patent No.: US 12,558,518 B2
(45) Date of Patent: Feb. 24, 2026

(54) CATHETER COMPRISING A FLEXIBLE FLAT CABLE AND FPCB AND METHOD FOR PRODUCING IT

(71) Applicant: Berner Fachhochschule, Technik und Informatik, Biel (CH)

(72) Inventors: Thomas Niederhauser, Oberwangen b. Bern (CH); Gerhard Kuert, Magglingen (CH); Marcel Jacomet, Lengnau (CH); Reto Andreas Wildhaber, Olten (CH)

(73) Assignee: Berner Fachhochschule, Technik und Informatik, Biel (CH)

( * ) Notice: Subject to any disclaimer, the term of this patent is extended or adjusted under 35 U.S.C. 154(b) by 1224 days.

(21) Appl. No.: 17/401,689

(22) Filed: Aug. 13, 2021

(65) Prior Publication Data

US 2022/0047845 A1     Feb. 17, 2022

(30) Foreign Application Priority Data

Aug. 13, 2020    (EP) .................................... 20190962

(51) Int. Cl.
*H05K 1/02*        (2006.01)
*A61M 25/00*      (2006.01)
(52) U.S. Cl.
CPC ......... *A61M 25/0054* (2013.01); *H05K 1/028* (2013.01); *A61M 2025/0059* (2013.01); *H05K 2201/10151* (2013.01)
(58) Field of Classification Search
CPC ...... A61M 25/0054; A61M 2025/0059; A61B 2018/0016; A61B 18/1492; A61B 5/6852;
(Continued)

(56) References Cited

U.S. PATENT DOCUMENTS 6,447,314 B1    9/2002  Kato et al.
8,147,486 B2    4/2012  Honour et al.
(Continued)

FOREIGN PATENT DOCUMENTS

EP          3292885 A1      3/2018
EP          3315087 A1      5/2018
WO     2019211376 A1     11/2019

OTHER PUBLICATIONS

Benjamin et al., "Heart Disease and Stroke Statistics—2018 Update: A Report From the American Heart Association", Circulation, 2018, pp. e67-e492, vol. 137:12, American Heart Association, Inc.
(Continued)

*Primary Examiner* — Laura A Bouchelle
*Assistant Examiner* — Sarah Dympna Grasmeder
(74) *Attorney, Agent, or Firm* — The Webb Law Firm

(57) ABSTRACT

A catheter includes a catheter tube and a Flexible Printed Circuit Board, FPCB, wherein the FPCB covers essentially the catheter circumference for predetermined FPCB transducer segment length, especially at the distal portion, wherein the FPCB in the FPCB transducer segment includes a scaffold structure with a plurality of FPCB free spaces and one FPCB free surface portion creating maximum mechanical stability with the least amount of material and a FPCB scaffold structure which ensures maximum flexibility. The FPCB includes transducer patches which are connected by traces on the straight scaffolds of the scaffold structure. The FPCB free spaces are configured for preventing, circumventing and/or compensating the kinking behavious of the catheter tube.

20 Claims, 18 Drawing Sheets

(58) Field of Classification Search
CPC ............. A61B 2562/166; H05K 1/028; H05K 2201/10151; H05K 2201/056; H05K 1/0283; H05K 1/189; H05K 2201/09063
See application file for complete search history.

(56) References Cited

U.S. PATENT DOCUMENTS

| | | |
|---|---|---|
| 2012/0271135 A1 | 10/2012 | Burke et al. |
| 2014/0378803 A1 | 12/2014 | Geistert et al. |
| 2015/0005799 A1 | 1/2015 | Lindquist et al. |
| 2016/0228061 A1 | 8/2016 | Kallback et al. |
| 2016/0287863 A1 | 10/2016 | Mercanzini et al. |
| 2017/0312023 A1 | 11/2017 | Harlev et al. |
| 2017/0348049 A1 | 12/2017 | Vrba et al. |
| 2018/0008821 A1* | 1/2018 | Gonzalez ............. H05K 3/4673 |
| 2018/0068759 A1* | 3/2018 | Bihler ...................... A61N 1/05 |
| 2018/0110562 A1 | 4/2018 | Govari et al. |
| 2020/0092991 A1* | 3/2020 | Viberg ................. H05K 1/0281 |

OTHER PUBLICATIONS

Gwon et al., "Fabrication and evaluation of an improved polymer-based cochlear electrode array for atraumatic Insertion", Biomed Microdevices, 2015, pp. 1-12, vol. 17:32, Springer Science+Business Media, New York.
Jeong et al., "A Miniaturized, Eye-Conformable, and Long-Term Reliable Retinal Prosthesis Using Monolithic Fabrication of Liquid Crystal Polymer (LCP)", IEEE Transactions on Bio-medical Engineering, 2015, pp. 982-989, vol. 62:3.
Seo et al., "Nerve cuff electrode using embedded magnets and its application to hypoglossal nerve stimulation", Journal of Neural Engineering, 2016, pp. 1-10, vol. 13:6.
Woods et al., "Long-term recording reliability of liquid crystal polymer µECoG arrays", Journal of Neural Engineering, 2018, pp. 1-29, vol. 15:6.

* cited by examiner

132

120

140

141

142

134

100

110

20

10

CATHETER COMPRISING A FLEXIBLE FLAT CABLE AND FPCB AND METHOD FOR PRODUCING IT

CROSS-REFERENCE TO RELATED APPLICATION

This application claims priority to European Patent Application No. 20 190 962.9 filed Aug. 13, 2020, the disclosure of which is hereby incorporated by reference in its entirety.

BACKGROUND OF THE INVENTION

Field of the Invention

The present invention relates to a catheter comprising a flexible flat cable and FPCB and a method producing it.

Description of Related Art

The increasing prevalence of patients with cardiovascular diseases and neurological disorders with the simultaneous medical progress has enforced the number as well as complexity of minimally invasive procedures over the past decades as shown by Benjamin Emelia J. et al., "Heart Disease and Stroke Statistics—2018 Update: A Report From the American Heart Association," Circulation, vol. 137, no. 12, pp. e67-e492, March 2018. Advanced diagnostic and therapeutic catheters have been developed for such interventions. The trend goes towards catheters that integrate multiple transducers, i.e. sensors and actuators, and maintain application-specific flexibility and steerability. However, design and manufacturing of high-density catheters is cumbersome due to typical soft material properties and small dimensions, respectively. The resulting manual manufacturing is labour intensive and prevents process automation and design extensions. To overcome these limitations, a novel catheter design and manufacturing process based on thin-film, flexible printed circuit boards (FPCB's) is proposed. Liquid crystal polymer (LCP) has been investigated as FPCB for lamination with thermoplastic tubular elastomers to build high-density catheters. LCP has recently gained much attention for various biomedical applications such as the encapsulation of micro-electrocorticographic arrays shown by V. Woods et al., "Long-term recording reliability of liquid crystal polymer µ ECoG arrays," J. Neural Eng., vol. 15, no. 6, p. 066024, 2018. The use of LCP in multi-channel cochlear electrode arrays was introduced in T. M. Gwon et al., "Fabrication and evaluation of an improved polymer-based cochlear electrode array for atraumatic insertion," Biomed. Microdevices, vol. 17, no. 2, p. 32, February 2015. The application of LCP in small and light-weight retinal prostheses was shown in J. Jeong et al., "A Miniaturized, Eye-Conformable, and Long-Term Reliable Retinal Prosthesis Using Monolithic Fabrication of Liquid Crystal Polymer (LCP)," IEEE Trans. Biomed. Eng., vol. 62, no. 3, pp. 982-989, March 2015. Furthermore magnetic nerve cuff electrodes based on LCP were presented in J. Seo et al., "Nerve cuff electrode using embedded magnets and its application to hypoglossal nerve stimulation," J. Neural Eng., vol. 13, no. 6, p. 066014, 2016. Most of these applications share LCP as durable material with excellent mechanical and electrical properties such as mechanical stability, chemical inertness, and controllable stiffness vs. flexibility, low water absorption rate, and biocompatibility. Current manufacturing technologies for attaching a FPCB on a catheter rely on bonding, ultrasonic welding or other mechanical means that are known from US 2014/378803 A1 "Catheter and method for producing the same" for W. Geistert as well as from US 2016/228061 A1 "Low profile medical device with integrated flexible circuit and methods of making the same" for B. Källbäck and U.S. Pat. No. 8,147,486, "Medical device with flexible printed circuit" for K. Honour et al.

These processes usually result in catheters with a high stiffness because the edges have been glued or welded together in order to establish a tubular structure. Such catheters are limited to specific applications where no bendability and flexibility is required.

The majority of the bonding processes are promoting additives as key element to adhere the FPCB, which are generally sensitive to environmental conditions and additive dosage. Furthermore, the presence of adhesives is undesirable in a cleanroom setting during manufacturing.

US 2015/005799 A1 "Renal nerve modulation balloon having improved robustness" for J. S. Linguist et al. uses a laser etching onto the surface of the catheter to reach improved adhesion properties while bonding.

US 2012/0271135 "Flexible electrode assembly for insertion into body lumen or organ" for J. A. Burke et al. discloses the insertion of a FPCB in a single or multi lumen tube and it's expansion on the distal end of the catheter. The presented catheter is configured to be used as a diagnostic device for the detection of paroxysmal arrhythmias.

EP 3 315 087 A discloses a catheter with an insertion tube, a flexible substrate and one or more electrical devices. The insertion tube is configured for insertion into a patient body. The flexible substrate is configured to wrap around a distal end of the insertion tube and includes electrical interconnections. The electrical devices are coupled to the flexible substrate and are connected to the electrical interconnections. The PCB sheet has a plurality of irrigation holes arranged in circumferential rows and lines in the longitudinal direction of the PCB sheet, wherein micro-electrodes are provided on places where no irrigation holes are provided, i.e. interrupting in the FIG. 4 of EP 3 315 087 two rows on one line for every micro-electrode.

WO 2019/211376 A1 "Method for producing a catheter comprising a FPCB" discloses a manufacturing method for a catheter that is based on a FPCB made from LCP and a TPU base substrate. The adhesion strength of the LCP is increased by the introduction of adhesion promotion holes on the edge of the FPCB shown in FIG. 2C of WO 2019/211376 A1.

EP 3 315 087 A1 "Catheter distal end made of plastic tube and flexible printed circuit boards" shows an ablation catheter tip made of a LCP based FPCB that is wrapped around the catheter tip in a semi-spherical shape.

EP 3 292 885 A1 "Stretchable electrode conductor assembly and medical implant" discloses the concept of a catheter comprising the support of the electrode arrangement from an essentially non-stretchable material that exerts only small tensile forces on the interface to the conductor tracks when the arrangement is stretched. This can ensure a longer life during operation, even with frequent stretching by relatively large amounts. The required stretchability of the arrangement is realized as a whole by cutting the support in a zigzag or meandering pattern to adapt it to the contour of the conductor track(s). Thus, the stretchability of the support, like that of the conductor tracks, is realized by the special geometric configuration.

U.S. Pat. No. 6,447,314 uses an FPC, especially an enrolled FPC, for providing contacts at the opposite sides and discloses that it is necessary to bend it only; the FPCB is not extensible as such and needs a configuration like in FIG. 4C of said document to accommodate different lengths.

US 2018/008821 A1 discloses thin film devices and methods of manufacturing and implanting the same. This comprises a shaped insulator having an inner surface, an outer surface, and a profile shaped according to a selected dielectric use. A layer of conductive traces is fabricated on the inner surface of the shaped insulator using biocompatible metallization. An insulating layer is applied over the layer of conductive traces. An electrode array and a connection array are fabricated on the outer surface of the shaped insulator and/or the insulating layer, and the electrode array and the connection array are in electrical communication with the layer of conductive traces to form a flexible circuit.

US 2017/348049 A1 discloses various devices and methods for modulating targeted nerve fibers or other tissue as well as for cooling energy delivery members, wherein these systems may be configured to access tortuous anatomy of or adjacent hepatic vasculature.

US 2018/068759 A1 shows a stretchable electrode conductor arrangement, US 2017/312023 A1 discloses ablation systems and methods using a catheter including one or more image sensors, and US 2016/287863 A1 shows microelectrode array devices for electrical stimulation.

SUMMARY OF THE INVENTION

Based on this prior art, it is an object of the present invention to provide an improved concept of and a method to produce a medical device, especially a catheter, comprising passive and/or active transducers with/without electronic components providing the desired catheter bendability, pushability, torquability and kinking compensation or prevention. One or multiple transducers can be sensors, actuators, or both.

Although it is mentioned in prior art documents that such medical devices as catheters comprise a FPCB or an FPC, it is to be noted that they comprise transducers, e.g. sensors, where the wording FPCB is correct, and connecting portions as well as between distant transducers positioned on a flexible printing circuit as well as connecting portions which should be qualified as FFC for flexible flat cable. But since connector portions can be seen as part of a printed circuit board, the entire segment with transducers and connections is mentioned as FPCB transducer segment This object is achieved with a catheter comprising a catheter tube and a FPCB transducer segment, wherein the FPCB transducer segment comprises a scaffold structure with a plurality of FPCB surrounded free spaces, a FPCB free surface portion and predetermined placed transducer patches, wherein the FPCB covers essentially the catheter circumference for the length of the FPCB transducer segment with the exception of the FPCB free surface portion, wherein these features give the catheter a wide variety of different configuration possibilities to meet requirements on mechanical deformation, transducer efficiency and signal quality.

The feature that the FPCB covers essentially the catheter circumference for the length of the FPCB transducer segment with the exception of the FPCB free surface portion meaning that the FPCB in the FPCB transducer segment can be seen as having a sheet form with a distal and a proximal side and two lateral sides which are mainly directed in longitudinal direction of the catheter but these lateral sides never contact each other but maintain in-between a FPCB free surface portion, which is not necessarily following a straight line. The leftmost portion of the left side can be positioned in a recess of the right side of the FPCB scaffold what is in line with a polygonal shape of the scaffold.

Such a catheter comprises a catheter tube, preferably a thermoplastic polymer tube and a FPCB, preferably made of LCP, wherein the FPCB partially covers the catheter circumference on predetermined segments along the longitudinal axis of the catheter tube. On the body-exposed distal segment of the catheter the FPCB is conceived as interlinked, regular scaffold structure with a plurality of FPCB free spaces providing the FPCB covered segment with the maximum stability, while using the minimal amount of material. The resulting functional scaffold structure ensures the desired bendability, pushability and torquability, prevention or compensation of catheter kinking and the selective placement of one or multiple transducer patches The basic FPCB form is a scaffold structure in longitudinal and/or transverse direction that has sufficient FPCB free spaces. FPCB free space means that a straight line in the longitudinal or transverse direction has portions which are not occupied by FPCB material compared to portions occupied by FPCB material. Such FPCB free spaces ensure to fulfill catheter requirements with respect to bendability. The FPCB covered catheter segments and transducers are decreasing the catheter bendability. FPCB free spaces can be provided in both, the longitudinal and the transverse direction to ensure the desired catheter bendability in said directions. The longitudinal and/or transverse symmetry further allows reducing the amount of freestanding FPCB segments and concurrently improves the catheter stability. The FPCB free space can have the shape of a polygon, whereby multiple FPCB corners, internal angles and edges constitute the specific shape of the cut-out. The FPCB edges and FPCB corners can be arranged in a specific shape according to the mechanical requirement of the catheter design. The FPCB free spaces can be shaped regular, which means axialsymmetric with FPCB edges of similar length or irregular which means non axial-symmetric with FPCB edges of different lengths.

It is an advantage for the flexprint when it is based on a hexagonal or diamond basic pattern which serves as the basis for all openings which was derived by structural-mechanical simulation. The openings are hexagonal or diamond in shape which allows an improved bendability and they are especially created based on a FEM simulation.

Transducer patches are especially provided on the FPCB basis hexagonal or diamond shape pattern, but it is also possible that the extend beyond the hexagonal or diamond shape FPCB basic film into the inner hexagonal or diamond shaped openings, which does not hinder the bendability. It is possible to have a connecting FPCB web between the transducer patches on the FPCB basic film.

In one embodiment the smallest element of the herein described scaffold structure is a hexagonal axial-symmetrical honeycomb FPCB free space that can be described by a defined set of parameters like the internal angles alpha, beta and the polygon height h. These honeycombs can form regular or irregular spaced clusters in order to create a scaffold structure on which transducer patches can be placed. The honeycomb shaped FPCB free space can be rotated in a desired direction according to the required bending behaviour of the complete scaffold structure. In the herein described document the honeycomb shaped FPCB free space was rotated by 90 degrees. In other words, the direction of a predetermined honeycomb defining line can be oriented not only along the longitudinal axis of the catheter but also in any angle between 0 and 90 degrees.

Another embodiment of the invention is a modified version of the honeycomb, namely an ellipsoid shaped FPCB free space in the transverse direction, which allows for improved bending in the longitudinal direction. Through multiple cuts that result in FPCB free spaces the catheter gets bendable in a multitude of directions. The ellipsoid shaped FPCB free space can have any quantity or orientation and can gradually change dimensions along the catheter axis to accommodate for various bending requirements. The FPCB corners can be undercut or overcut to diminish the stress peaks during bending. An ellipsoid outline can be added to the FPCB edges of the FPCB (in order to disseminate stress on the FPCB and improve bendability of the catheter. The ellipsoid shaped FPCB free spaces has preferably a cut-out that is a larger than the dimensions of the natural kinking of the catheter that occurs when no LCP is present on the circumference. This kinking compensated cut-out is preventing stress peaks in the LCP material and ensures a bending angle from 0 to −90 degree without LCP delamination.

Although the FPCB free portion between the opposite edges of the FPCB segment is direction in the longitudinal direction of the medical device. It is possible that the FPCB segment has an outer circumference of a parallelogram and therefore the FPCB free portion will be essentially helix-shaped, since also a parallelogram FPCB segment would follow an essential helix-shape around the lateral surface of the cylinder of the catheter.

Electronic components can be placed on the upper or bottom side of the FPCB and the FPCB can subsequently be thermoformed on the interior or the exterior wall of the catheter tube. The four presented options to place electronic components allow for the seamless integration of electronic components of any size, without interfering with the outside of the catheter. The electronic components can comprise transducers, i.e. sensors and actuators, multiplexer, integrated circuits, amplifiers, coils or capacitors. To mitigate stresses on the FPCB during thermoforming of the flat electronic components, small FPCB openings are cut with a laser. Therefore, the electronic components, especially, if they have a certain height are preferably positioned on the side of the FPCB where such FPCB openings can be provided to accommodate the thickness of the associated electronic component, and to mitigate the rigidity of such an IC extending in the FPCB opening.

Further embodiments of the invention are laid down in the dependent claims.

BRIEF DESCRIPTION OF THE DRAWINGS

Preferred embodiments of the invention are described in the following list with reference to the drawings, which are for the purpose of illustrating the present preferred embodiments of the invention and not for the purpose of limiting the same. In the drawings

6

Figure 3:
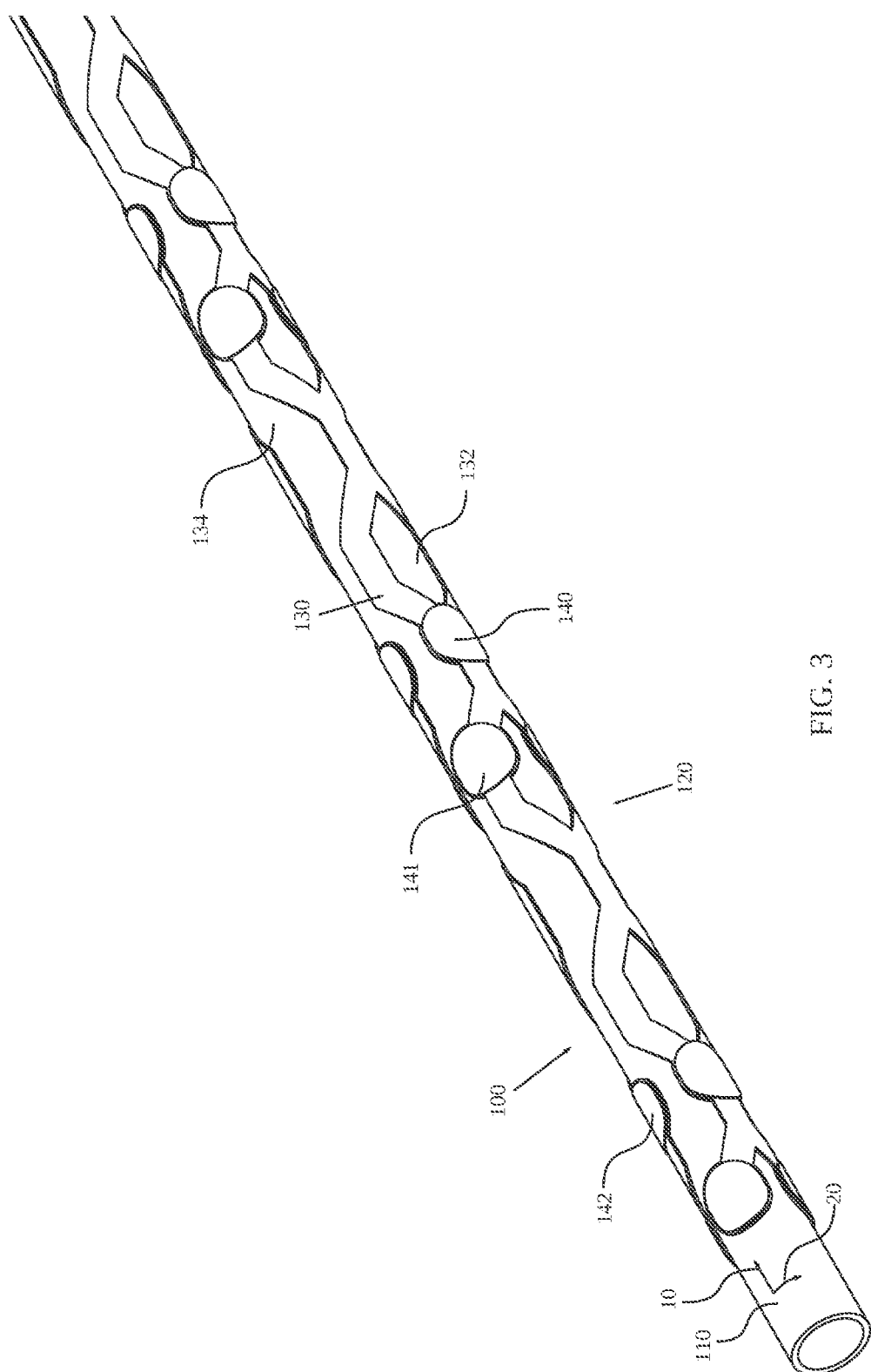
FIG. 3 shows a perspective view of a catheter segment comprising a FPCB according to a second embodiment of the invention.
Figure 4:
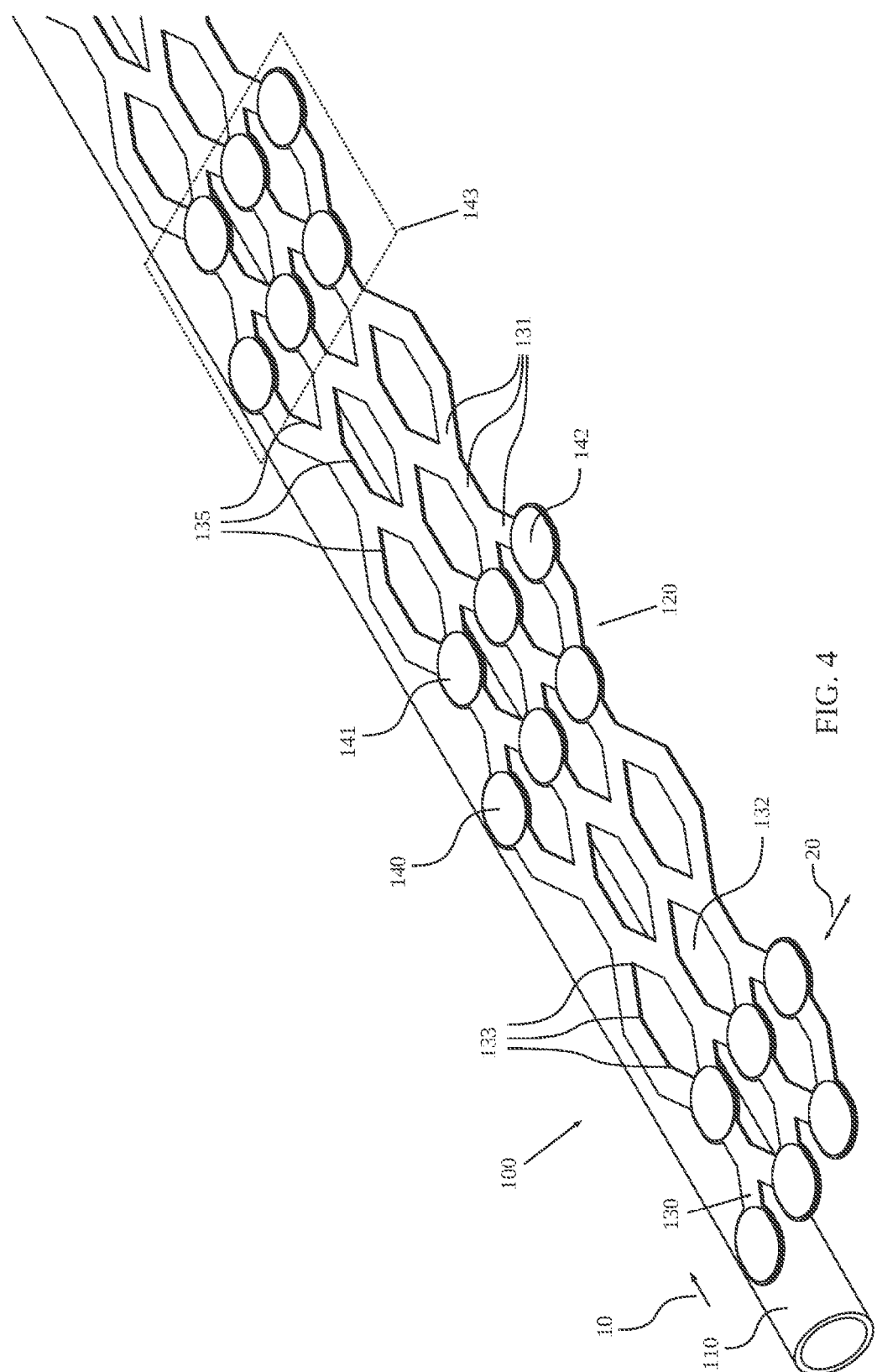
FIG. 4 shows the catheter tube of FIG. 3 with the FPCB separated from the tube.
Figure 5:
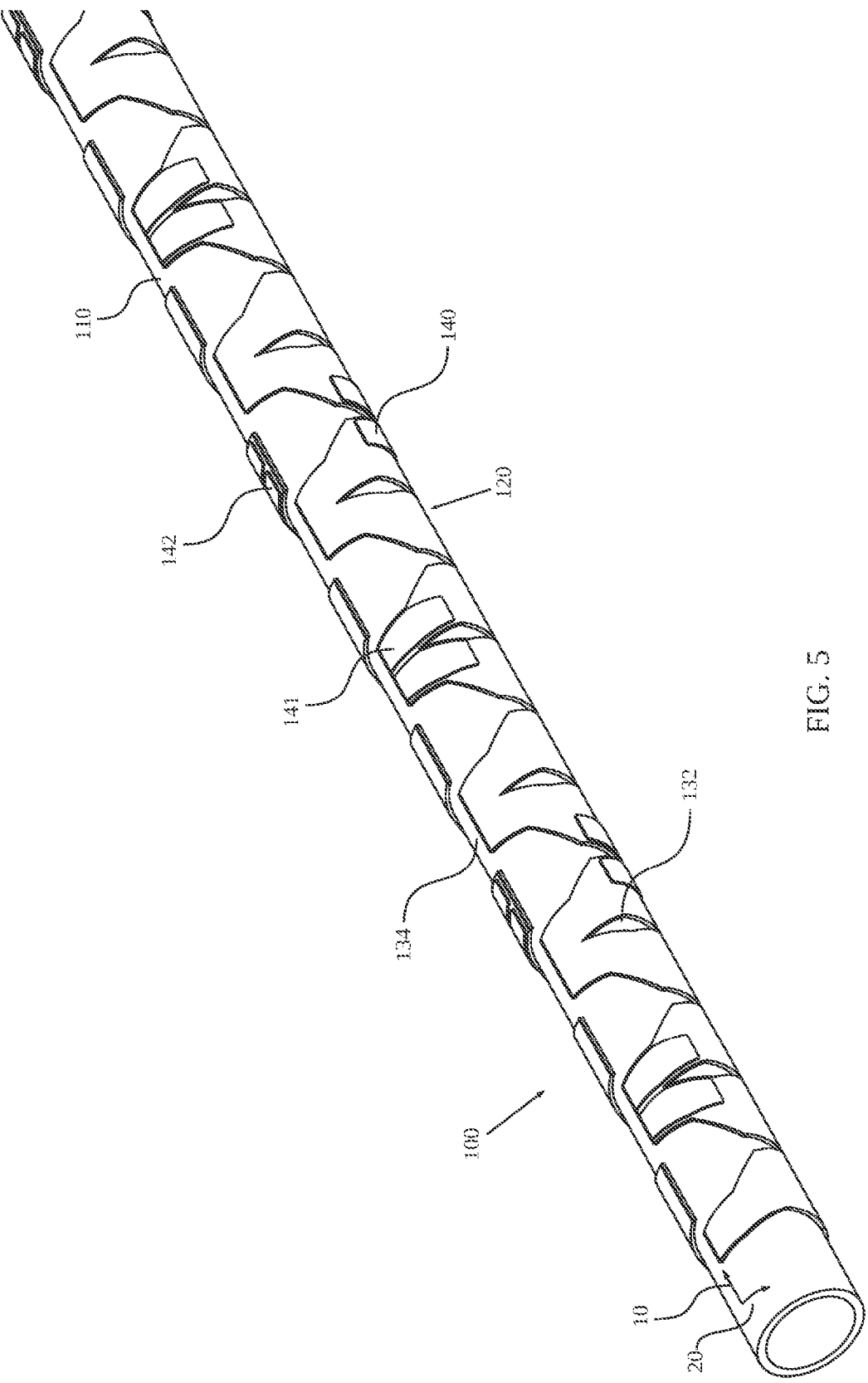
FIG. 5 shows a perspective view of a catheter segment comprising a FPCB according to a third embodiment of the invention.
Figure 6:
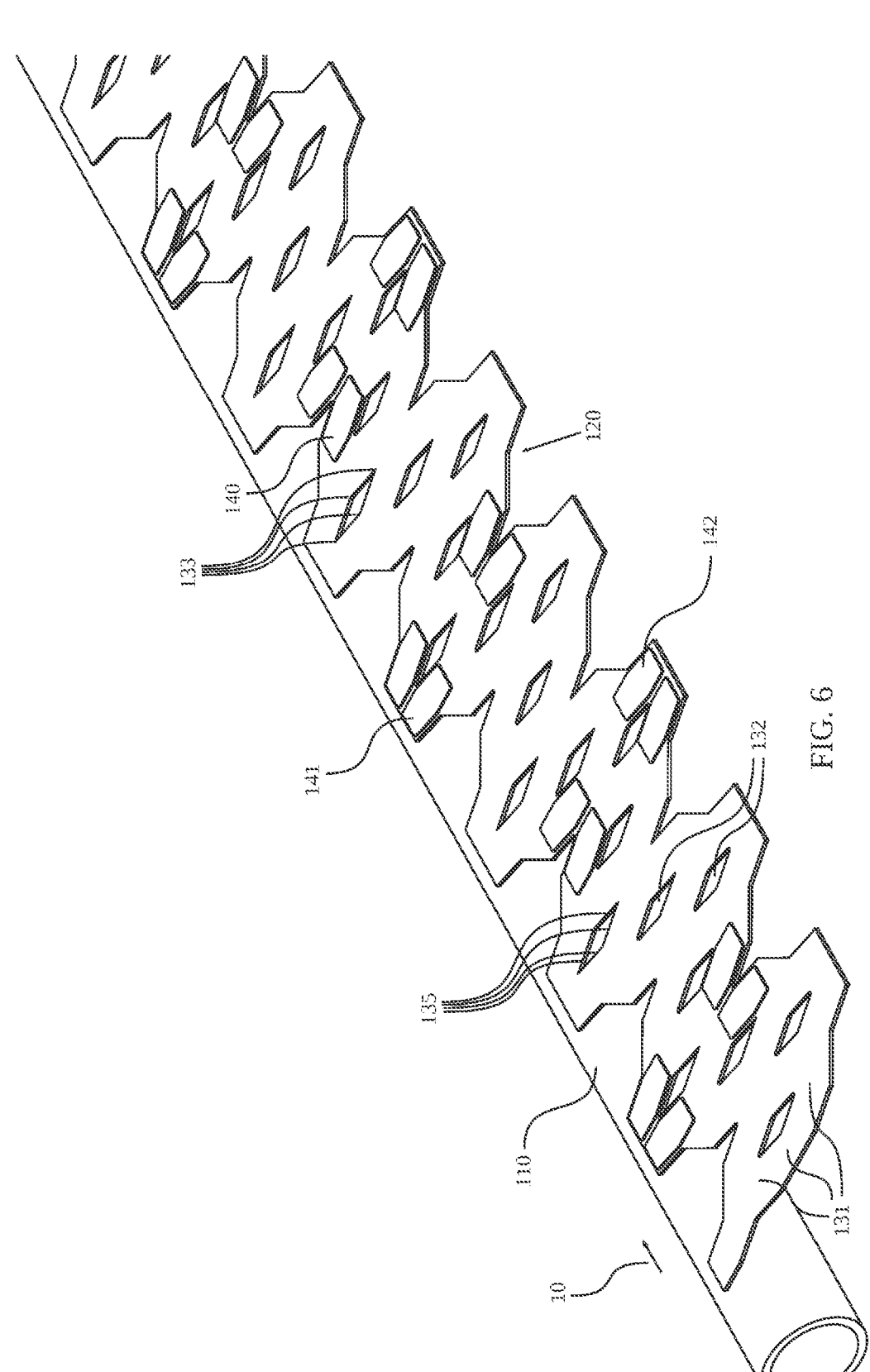
Figure 7:
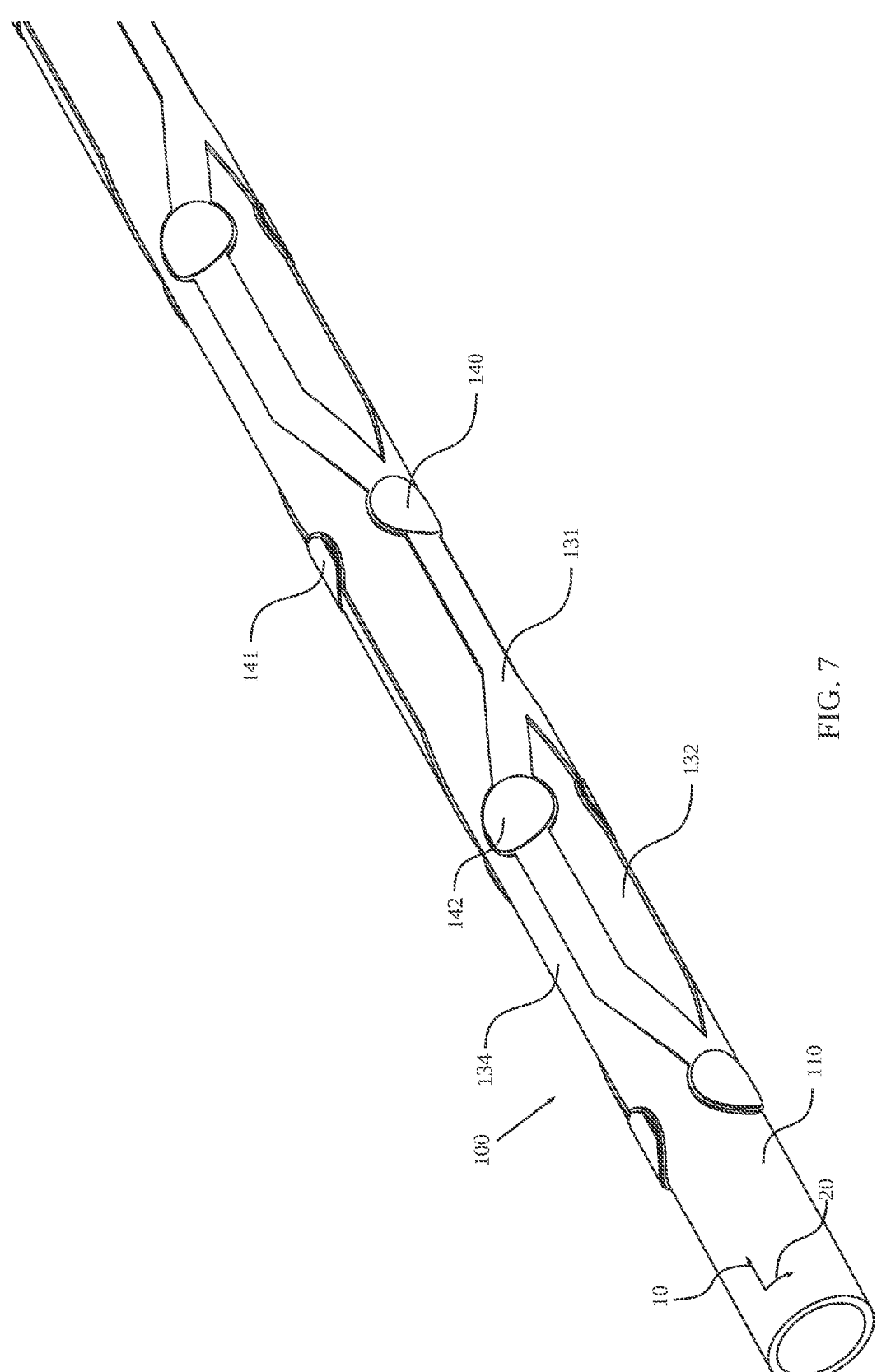
Figure 8:
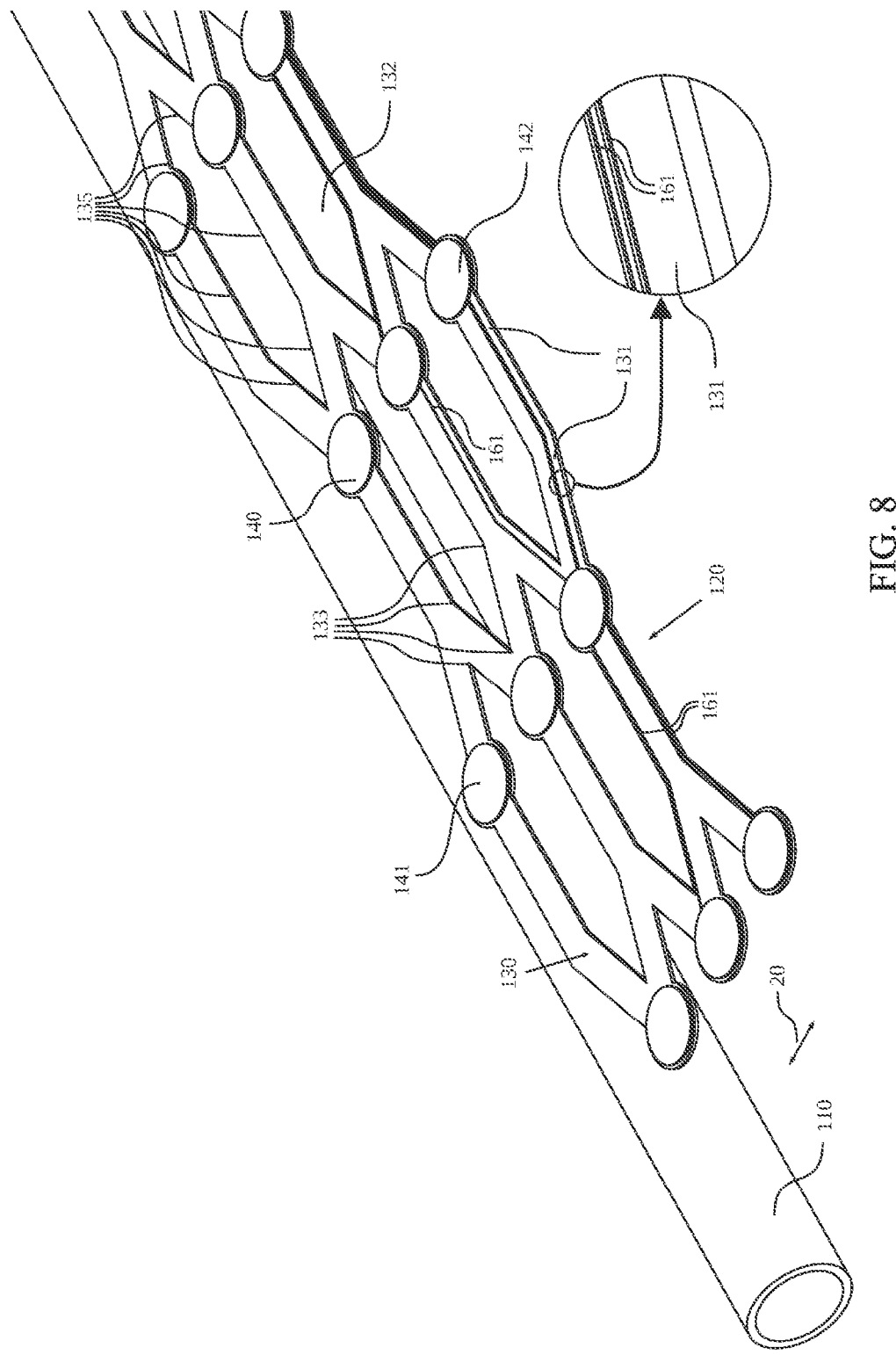
Figure 9:
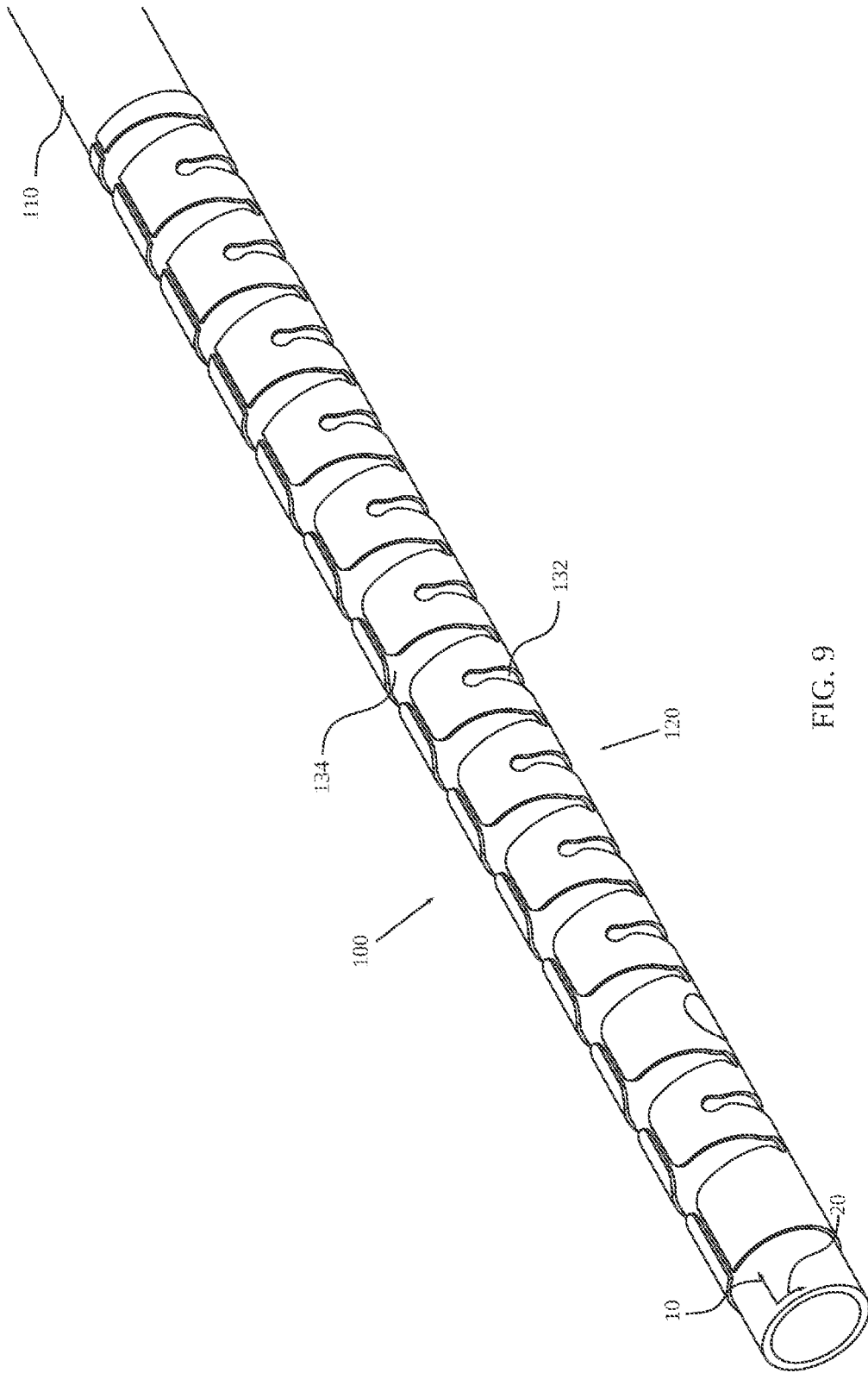
Figure 10:
Figure 11:
Figure 12:
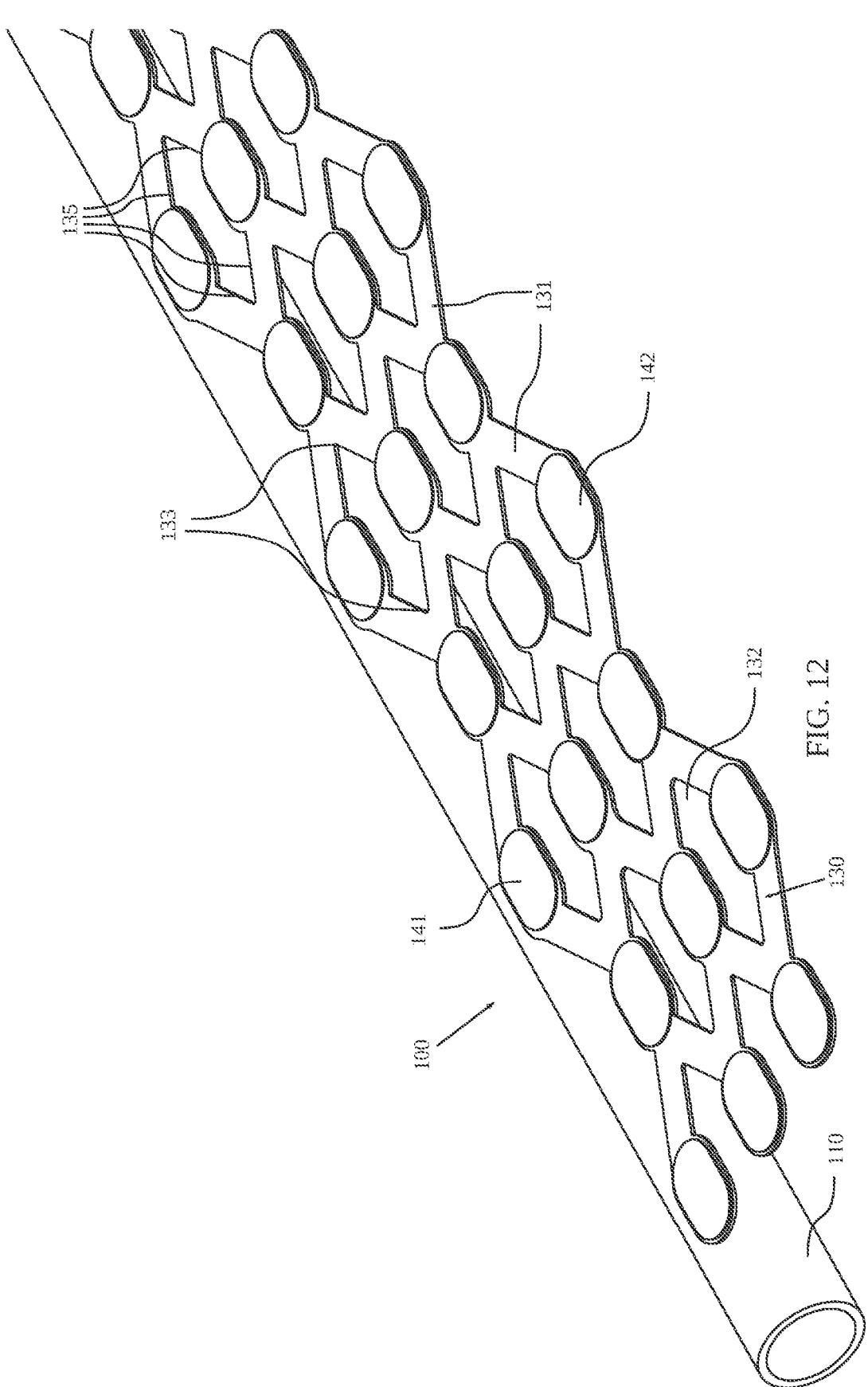
Figure 13:
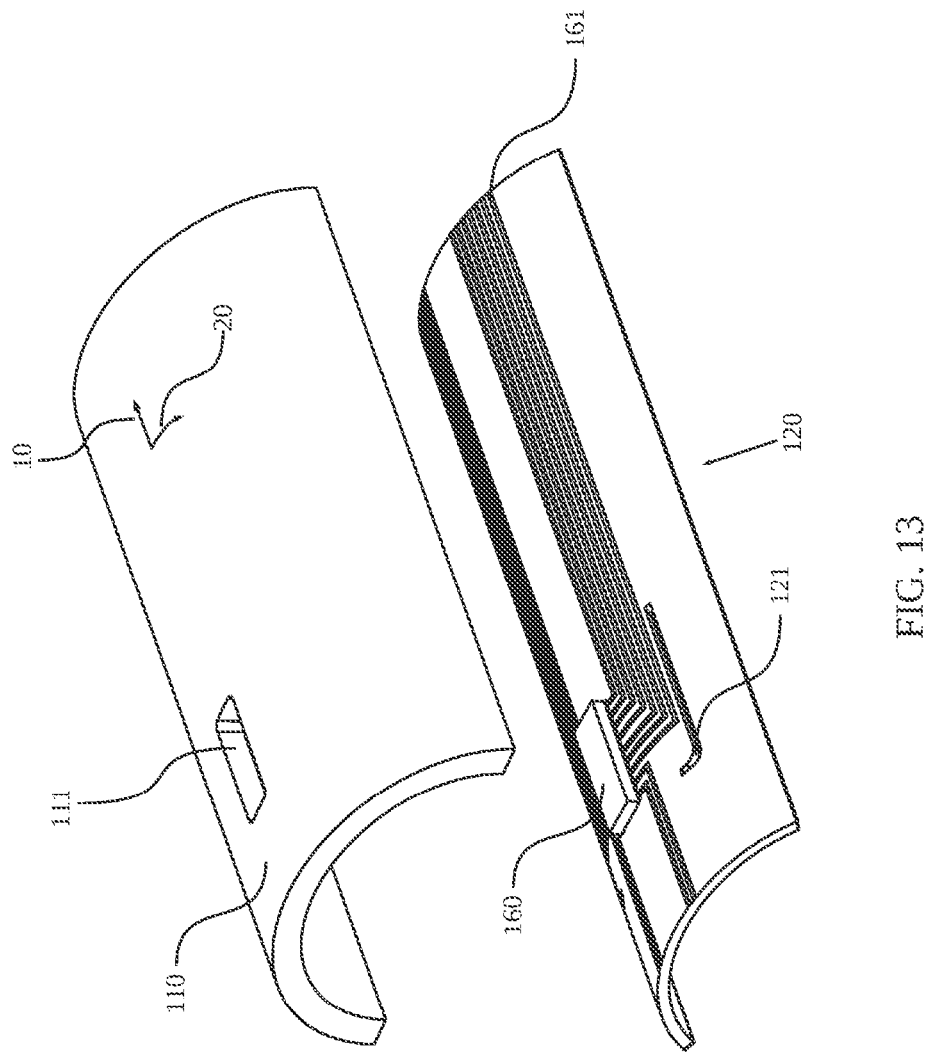
Figure 14:
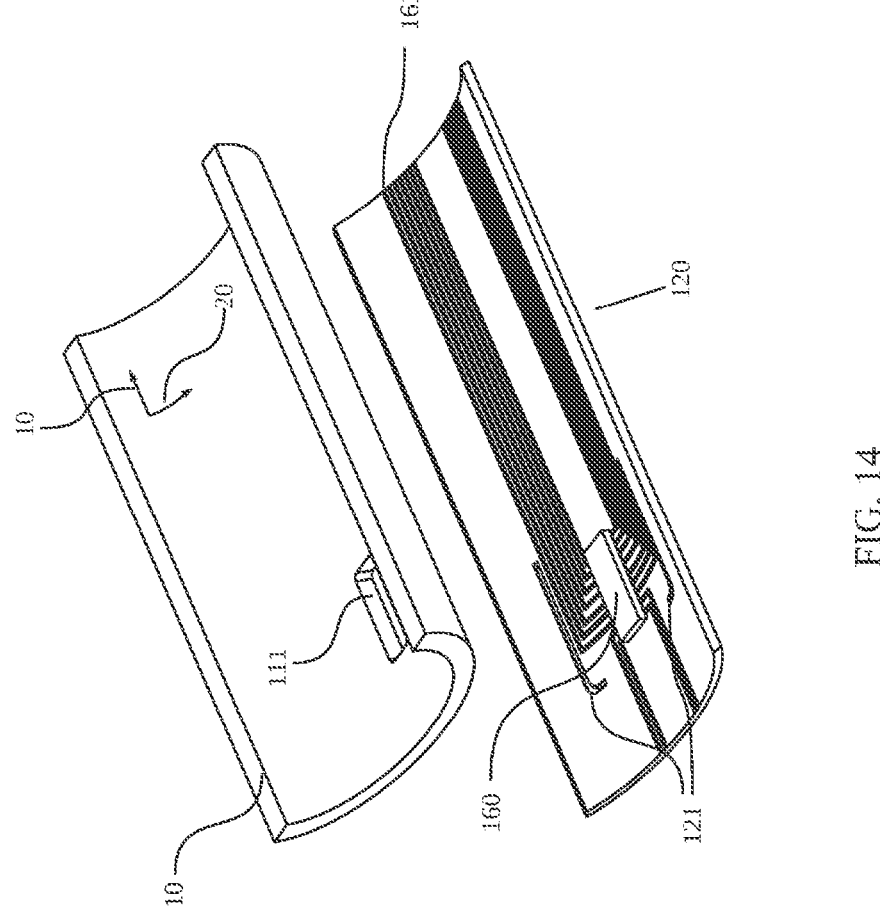
Figure 15:
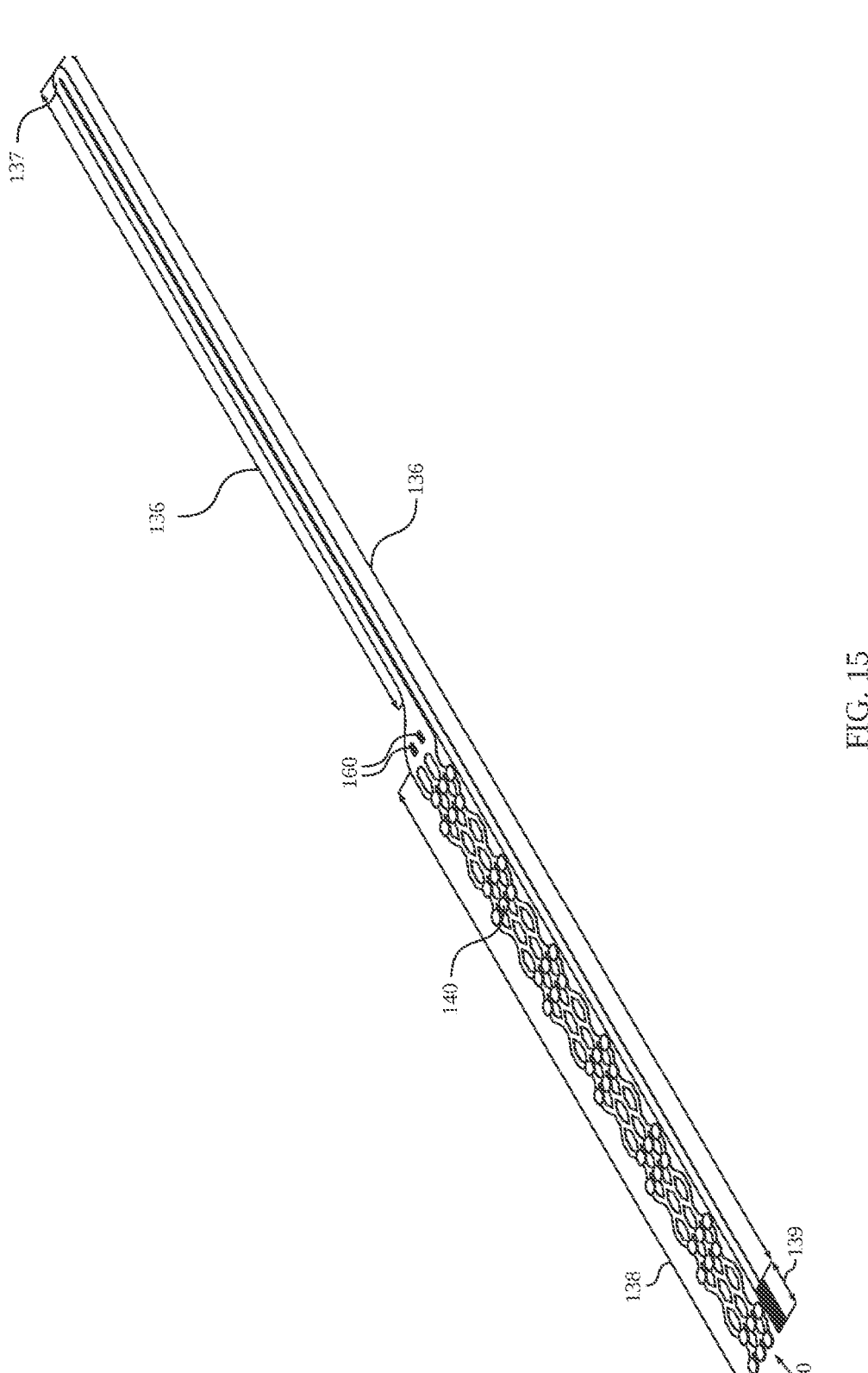
Figure 16:
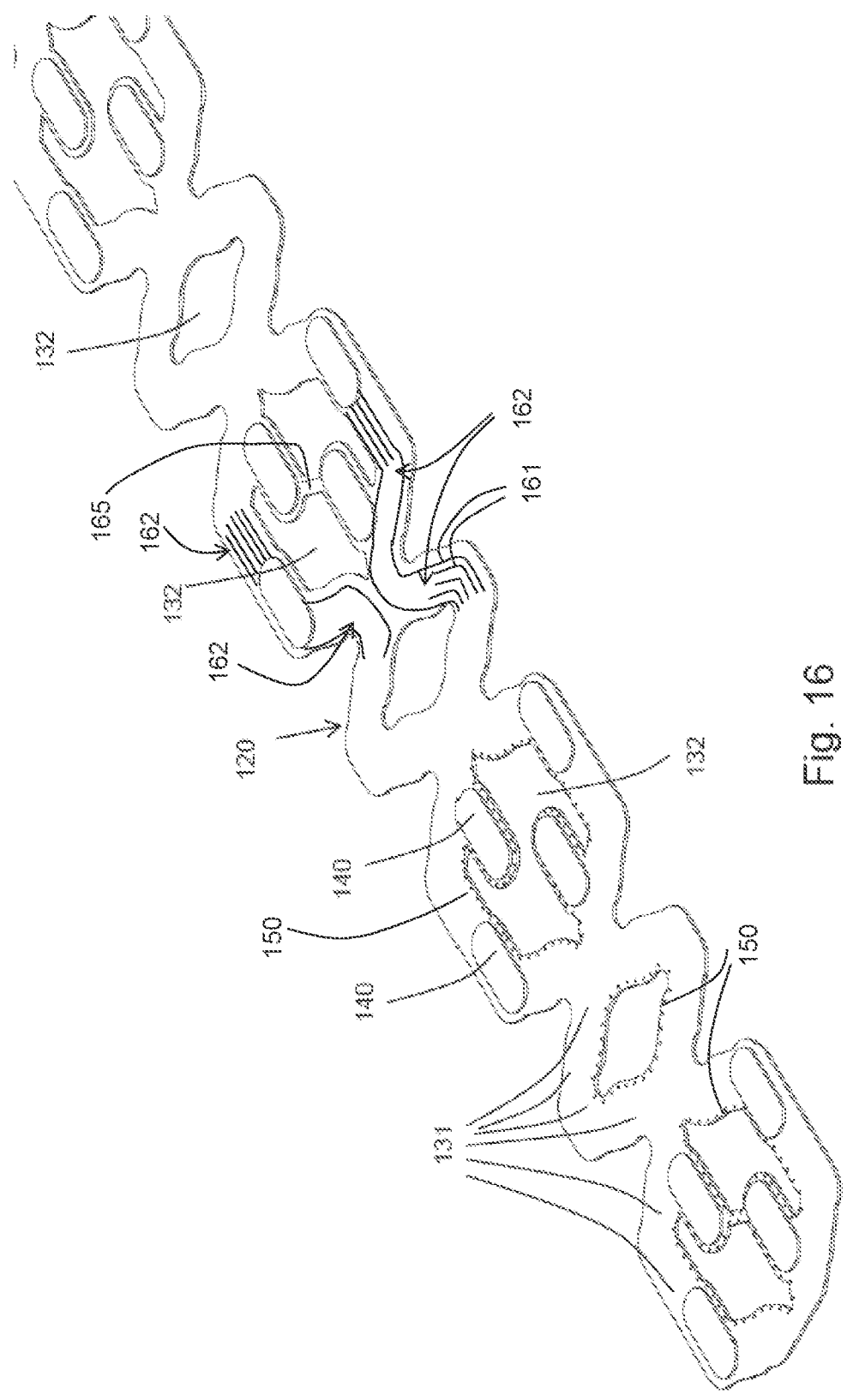
Figure 17:
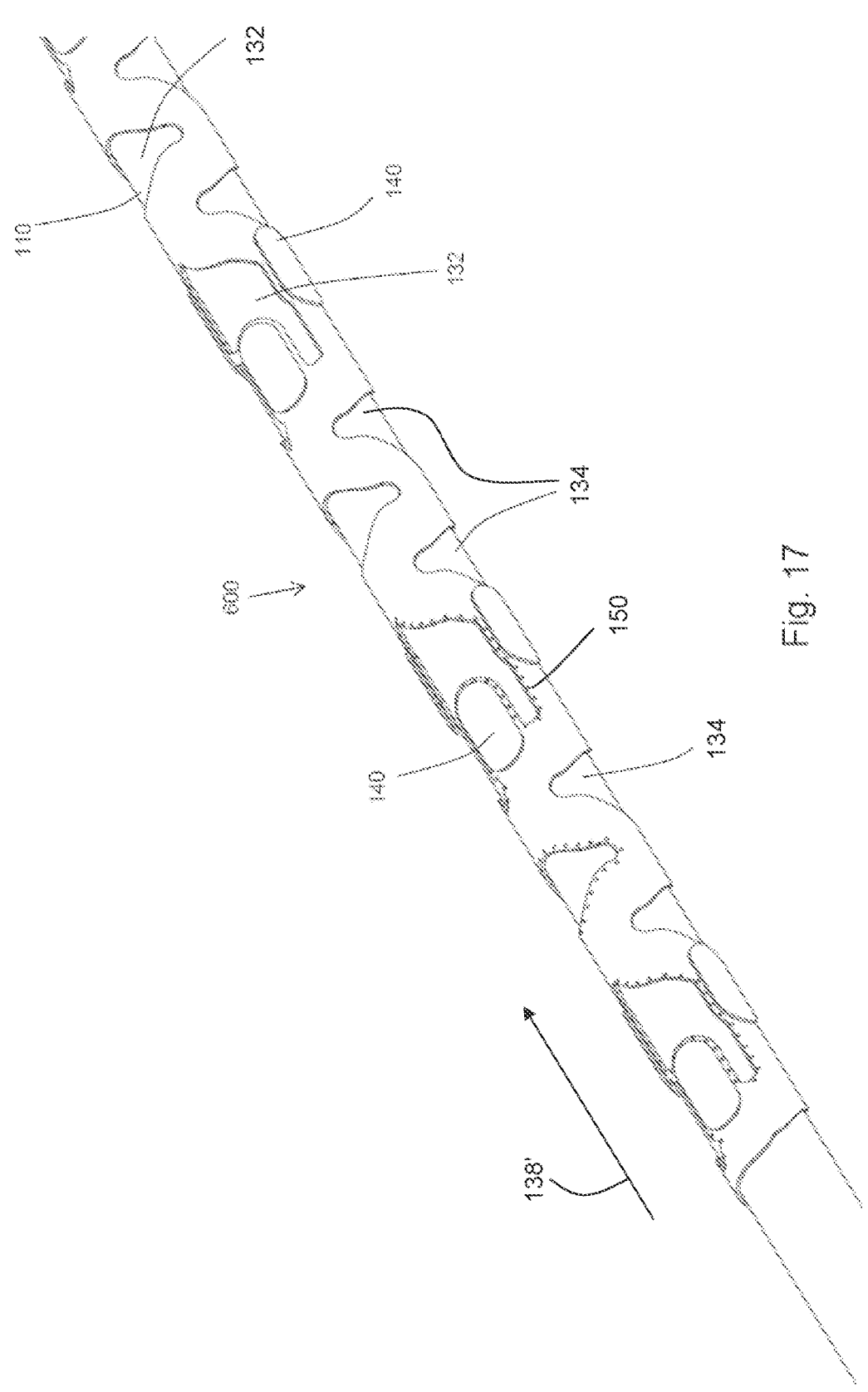
Figure 18:
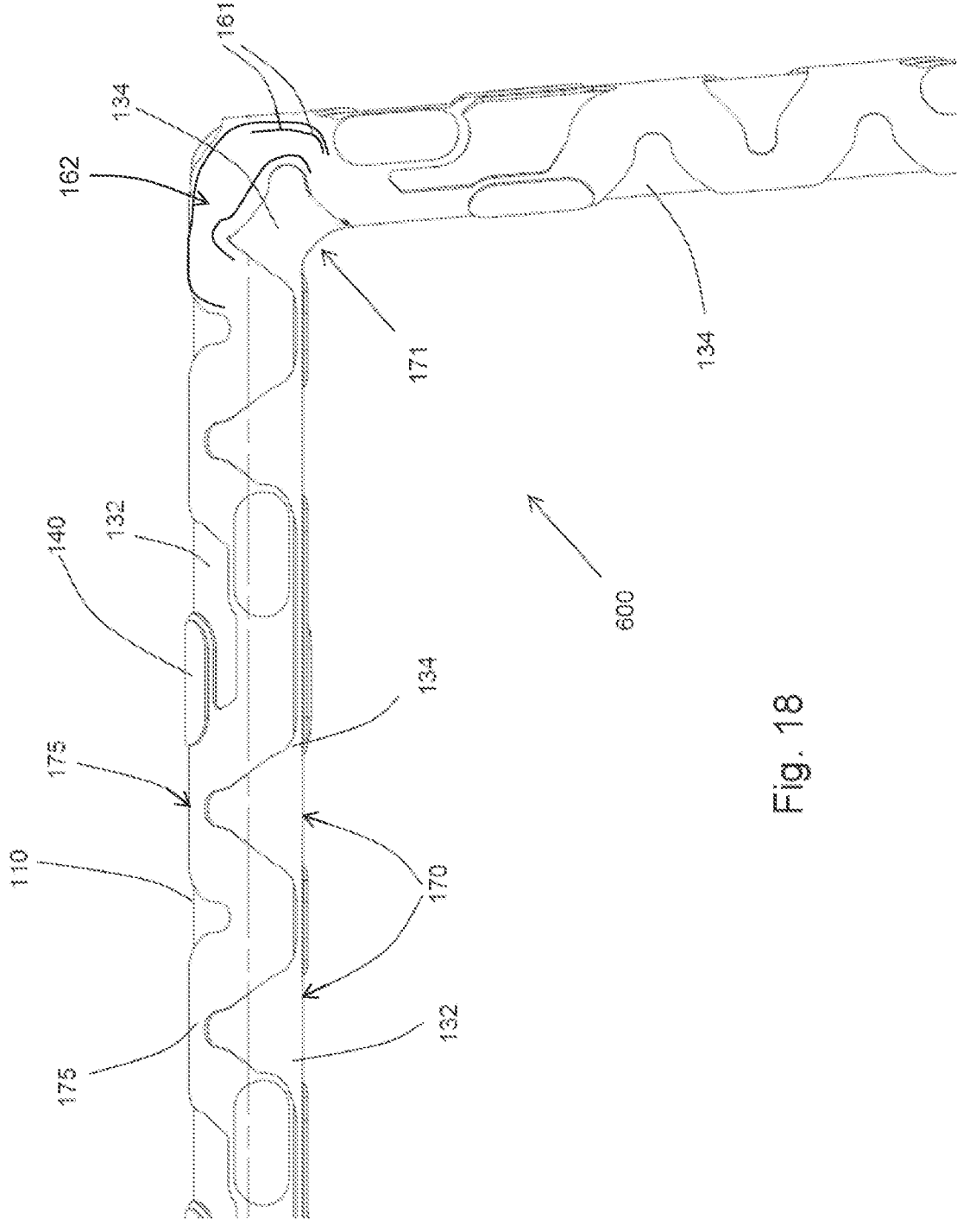

FIG. 6 shows the catheter tube of FIG. 5 with the FPCB separated from the tube;

FIG. 7 shows a perspective view of a catheter segment comprising a FPCB according to a fourth embodiment of the invention;

FIG. 8 shows the catheter tube of FIG. 7 with the FPCB separated from the tube together with a detail view of the traces of the FPCB;

FIG. 9 shows a perspective view of a catheter segment comprising a FPCB according to a fifth embodiment of the invention;

FIG. 10 shows the catheter tube of FIG. 9 with the FPCB separated from the tube;

FIG. 11 shows a perspective view of a catheter segment comprising a FPCB according to a first embodiment of the invention;

FIG. 12 shows the catheter tube of FIG. 11 with the FPCB separated from the tube;

FIG. 13 shows a section of a catheter segment that has an electronic component placed on the FPCB inside the catheter lumen;

FIG. 14 shows a section of a catheter that has an electronic component placed on the FPCB outside of catheter tube;

FIG. 15 shows a full view of the catheter presented in FIG. 3 and FIG. 4, wherein the outline of the FPCB is subdivided into multiple parts that constitute a transducer, tail and connector segment;

FIG. 16 shows a schematic drawing of a FPCB sheet for an embodiment similar to FIG. 3;

FIG. 17 shows a perspective view of the FPCB sheet of FIG. 16 wound around a catheter segment; and FIG. 18 shows a perspective view of the catheter of FIG. 17 with the surrounding FPCB sheet bent in an exaggerated angle.

DESCRIPTION OF THE INVENTION

Figure 1:
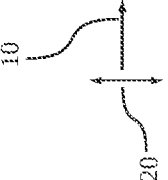
FIG. 1 shows a schematic drawing of a FPCB sheet for an embodiment similar to FIG. 3.

FIG. 1 shows a schematic drawing of a FPCB sheet for an embodiment similar to FIG. 3. The FPCB 120, i.e. the hexagonal shaped FPCB free spaces 132 are longer in the longitudinal direction 10 than in the transverse direction 20, i.e. the width of the FPCB sheet. The length of the hexagonal shaped FPCB free space 132 is determined by the internal angle alpha 36, beta 35 in longitudinal direction and the polygon height h 33 of the free space between the center of the FPCB free space 132 and the FPCB edge 135. The internal angle alpha 36, beta 35 and the polygon height 33 determine the form of the inner hexagonal FPCB free space 132. In addition is the form of the transducer patch 140 defined by the transducer patch width EW 38 and the transducer diameter ED 37. The distance from transducer to transducer patch 120 is defined by the transducer patch distance e1 31, whereby the distance of transducer patch 140 clusters is defined by e2 32. The transducer patch 120 distance to the edge of the FPCB is defined by wside 39. The FPCB surrounded free spaces 132 can also be named FFC surrounded free spaces, and the FPCB free surface portion 134 is a FFC free surface portion.

Figure 2:
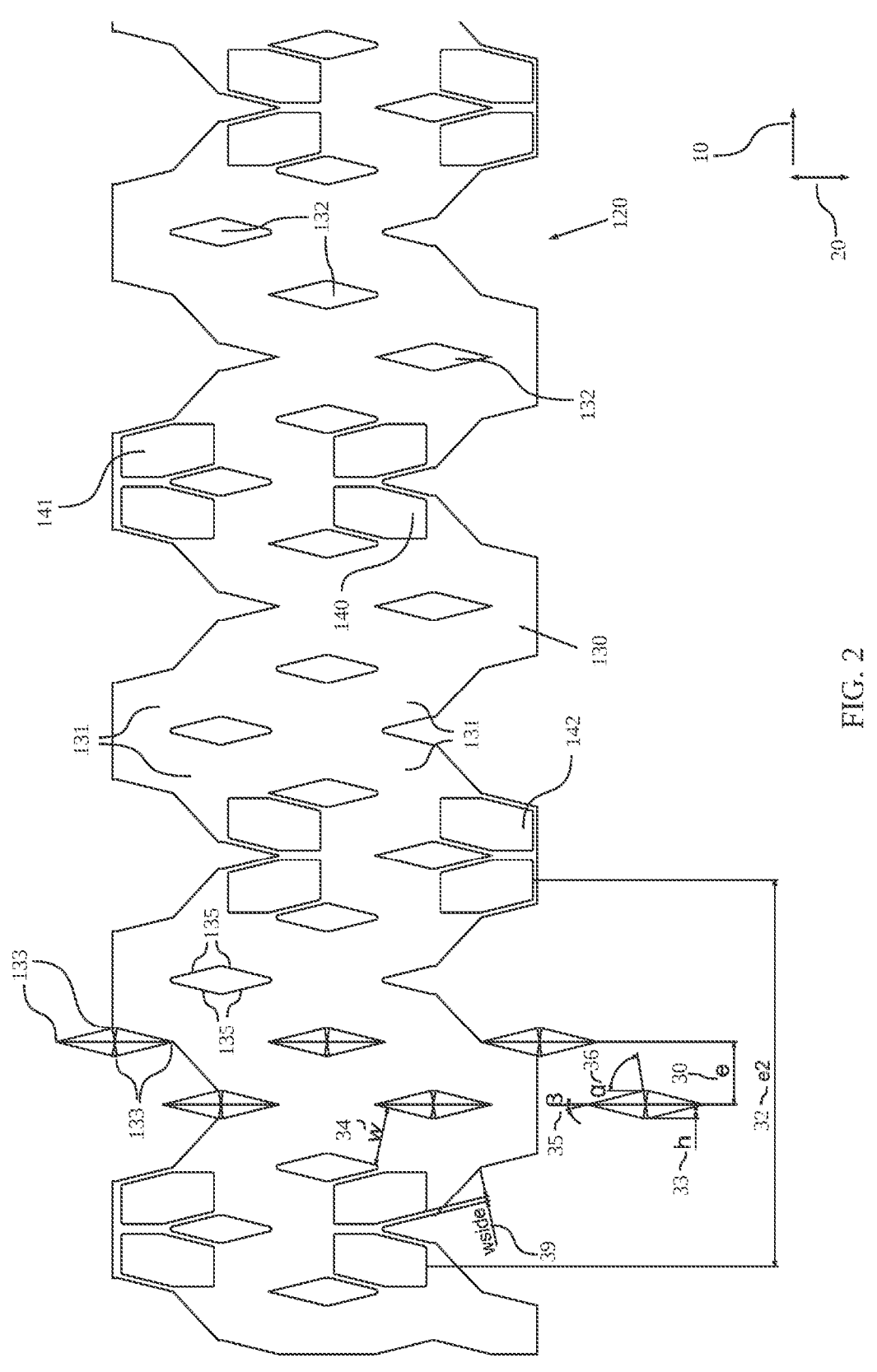
FIG. 2 shows a schematic drawing of a FPCB sheet for an embodiment similar to FIG. 5.

FIG. 2 shows a schematic drawing similar to FIG. 1 with the main difference that the FPCB free spaces 132 are turned 90 degrees and the internal angle alpha 36 and beta 35 have been changed to a different value. The transducer patches 140 have a different shape than shown in FIG. 1 but can also be of circular design.

FIG. 3 shows a perspective view of a catheter 100 with a flexible printed circuit board, i.e. FPCB 120 according to a first embodiment of the invention and FIG. 4 shows the catheter tube 110 of FIG. 3 with the FPCB 120 separated from the tube 110. The catheter 100 comprises at least the catheter tube 110 based on a polymer, preferably a thermoplastic polymer onto which the FPCB 120 was thermobonded on its circumference.

FIG. 4 shows that the FPCB 120 can be provided initially as a separate flat sheet and comprises a scaffold structure 130 and a plurality of transducer patches 140. The scaffold structure 130 comprises straight scaffolds 131 forming a periodic structure of FPCB free spaces 132. Transducer patches 140 are attached or integrated intermittently on every second corner of the hexagons, i.e. for every hexagon three corners where the straight scaffolds 131 are connected comprise such a round transducer patch 140. The diameter of the transducer patches 140 is larger than the width of the straight scaffolds 131 and therefore can slightly protrude into the adjacent hexagon shaped FPCB free space 132. Within the embodiment of FIG. 4 the straight scaffold 131 in the longitudinal direction 10 of the catheter 100 are longer than the connecting inclined straight scaffolds 131 so that the FPCB free spaces 132 are lengthened in the longitudinal direction 10.

The straight scaffolds 131 comprise, where necessary, conductors, i.e. are in these portions flat flexible cables with one or more conductors, having a pitch which can e.g. be 0.1 millimeter, provided on the flat and flexible LCP base. These conductors are distributed inside different straight scaffolds 131 according to the wiring needs for the transducers to be used on the transducer patches 140. Therefore, wiring conductors can bifurcate at inner FPCB free spaces 132 and come together (again) when the three straight scaffolds 131 meet again at the node points. The conductors are shown as the traces 161 in FIG. 8, FIG. 13 or FIG. 14, and are embedded inside the FPCB 120. In other words, not all straight scaffolds 131 comprise a conducting connection 161 or wire and some comprise far more than one.

The scaffold structure 130 is cut out off a sheet having a predetermined length in the longitudinal direction 10 such that the transducers on the transducer patches 140 have the necessary transducer distribution. The width of the sheet, i.e. in the transverse sheet direction 20, is predetermined so that in can be attached around the catheter tube 110 without portions of the left side of the FPCB 120 sheet overlapping portion of the right side of the sheet. In other words, as can be seen in FIG. 3, a continuous FPCB free surface portion 134 remains in the longitudinal direction 10. However, it is not necessary that the continuous FPCB free surface portion 134 comprises a straight line along the catheter 100. Here, transducer patches 141 and 142 at the left and right sheet border, respectively "block" such a straight line. In other words, every longitudinal line 10 at the circumference comprises portions of FPCB free spaces 132 and/or free spaces from the FPCB free surface portion 134 as well as portions of the straight scaffold 131 and at some places transducer patch 140.

This FPCB 120 sheet can be attached at the catheter tube 110 by the means of lamination or thermobonding. A segment of the FPCB 120 is cylindrically wrapped around the catheter tube 110 and adhered due to the temperature and pressure generated by the thermobonding process, whereby the melting temperature of the catheter tube 110 is exceeded.

The scaffold structure 130 is attached with the proximal end, which is during use of the catheter 100 the end portion of the catheter which is exterior of the patient via wires or attached FPCB traces 161 as known from the prior art. The FPCB connector segment 139 is usually provided at or near the distal end of the catheter and provides electrical connections via the traces 161 to the transducer patches 140. The transducer patches 140 can be made of gold and coated with platinum-iridium alloy for increased signal quality and biocompatibility.

The transducer patches 140 are shown as having a greater height than the adjacent straight scaffold 131. This existence of an adjacent height or the transducer patches 140 being flush with the scaffold structure 130 depend on the kind of transducer patches that are used. In any case, such thicker patches increase the rigidity of the structure, while the thinner straight scaffolds 131 and especially the FPCB free spaces 132 provides high flexibility in the longitudinal direction 10 which is necessary when the catheter 100 is bent at the upper and lower side of the curvature. The total FPCB free space is added up from the FPCB free spaces 132 inside the hexagons as well as the continuous FPCB free surface portion 134 between the non-contacting left and right sides from the originating printed flat FPCB 120.

The embodiment of FIG. 3 shows a sequence of two-hexagon-wide scaffold structures 130. The width can also be one, two or more polygons depending on the size of the scaffold structure 130 and the size of the catheter tube 110. This will be shown within the embodiment of FIG. 8. The embodiment of FIG. 4 shows transducer patch clusters 143, wherein the rectangle showing these six transducers patches 140 forming a cluster is only a virtual line to show that FIG. 4 shows three such clusters with intermittent FPCB-only scaffold portions. It is possible to have regular distribution of transducer patches or such transducer patch clusters 143 with intermittent areas of higher bendability due to less transducer patch 140 portions.

FIG. 5 shows a perspective view of a catheter 200 with a FPCB 120 according to a second embodiment of the invention and FIG. 6 shows the catheter tube 110 of FIG. 5 with the FPCB 120 separated from the tube 110. The catheter 200 comprises at least the catheter tube 110 based on a polymer, preferably a thermoplastic polymer onto which is affixed the FPCB 120.

The FPCB 120 can be provided initially as a separate flat sheet as shown in FIG. 6 and comprises a scaffold structure 130 and a plurality of transducer patches 140. The scaffold structure 130 comprises a straight scaffold 131 forming a periodic structure of hollow openings with an interior hollow space 132.

Pairs of hexagonal transducer patches 140 are attached or integrated intermittently on a predetermined number of straight scaffolds 131 pairs but also can be of circular design. The diameter of the transducer patches 140 is not larger than the width of the straight scaffold 131.

FIG. 7 shows a perspective view of a catheter 300 with a FPCB 120 according to a third embodiment of the invention and FIG. 8 shows the catheter tube 110 of FIG. 7 with the FPCB 120 separated from the tube 110. The catheter 300 comprises at least the catheter tube 110 based on a polymer, preferably a thermoplastic polymer onto which is affixed the FPCB 120. The FPCB 120 can be provided initially as a separate flat sheet as shown in FIG. 8 and comprises a scaffold structure 130 and a plurality of transducer patches 140. The scaffold structure 130 comprises straight scaffolds 131 forming a periodic structure of hollow hexagons with an interior hollow space 132. Transducer patches 140 are attached or integrated intermittently on every second corner of the hexagons, i.e. for every hexagon three corners where the straight scaffolds 131 are connected comprise such a round transducer patch 140. The diameter of the transducer patches 140 is larger than the width of the straight scaffolds 131 and therefore slightly project into the adjacent hexagonal hollow space 132. Within the embodiment of FIG. 7 the straight scaffolds 131 in the longitudinal direction 10 of the catheter 300 are longer than the connecting inclined straight scaffolds 131 so that the hexagonal hollow space 132 are lengthened in the longitudinal direction 10. The embodiment of FIG. 7 is therefore similar to the embodiment of FIG. 3.

FIG. 8 shows the traces 161 which are the electric conducting lines within the FPCB and shows that the scaffold structure effectively creates a scaffold of flexible flat cables being the straight elements 131 which may and which may not carry traces 161 depending on the use of the transducer patches 140 and the necessary connectivity. It is a preferred embodiment to provide different traces 161 and connections for different transducers in a distance one from another so that the traces are distributed over the width of the straight scaffolds 131. If there are two groups of traces 161 on a scaffold 131, they are positioned at the opposite edges of the scaffold. If there would be a third group, it would be positioned in the middle to maintain the greatest possible distance. The traces 161 are running through the transducer patches 140 (not shown in FIG. 8) and connect the transducers provided there.

FIG. 9 shows a perspective view of a catheter 400 with a FPCB 120 according to a fourth embodiment of the invention and FIG. 10 shows the catheter tube 110 of FIG. 9 with the FPCB 120 separated from the tube 110. The catheter 400 comprises at least the catheter tube 110 based on a polymer, preferably a thermoplastic polymer onto which is affixed the FPCB 120. The FPCB 120 can be provided initially as a separate flat sheet as shown in FIG. 8 and comprises a scaffold structure 130 and a plurality of transducer patches 140 that are integrated into the scaffold structure. The scaffold structure 130 comprises straight scaffolds 131 forming a periodic structure of hollow hexagons with an interior hollow space 132. Within the embodiment of FIG. 9 the straight scaffold structure 131 in the longitudinal direction 10 of the catheter 100 are far shorter than the connecting inclined straight scaffolds 131 so that the internal hollow space 132 are lengthened in the transverse direction 20.

FIG. 11 shows a perspective view of a catheter 500 with a FPCB 120 according to a fifth embodiment of the invention and FIG. 12 shows the catheter tube 110 of FIG. 11 with the FPCB 120 separated from the tube 110. The catheter 500 comprises at least the catheter tube 110 based on a polymer, preferably a thermoplastic polymer onto which is affixed the FPCB 120. The FPCB 120 can be provided initially as a separate flat sheet as shown in FIG. 10 and comprises a scaffold structure 130 and a plurality of transducer patches 140. The scaffold structure 130 comprises straight scaffolds 131 forming a periodic structure of hollow hexagons with an interior hollow space 132.

Transducer patches 140 are attached or integrated intermittently on every straight scaffold 131 in the longitudinal direction of the hexagons, i.e. for every hexagon the two opposite scaffolds in longitudinal direction 10 comprise such an oval transducer patch 140. The ovoid diameter of the transducer patches 140 is larger than the width of the straight scaffolds 131 and therefore slightly project into the adjacent FPCB free space 132.

Within the embodiment of FIG. 11 the straight scaffolds 131 in the longitudinal direction 10 of the catheter 500 are longer than the connecting inclined straight scaffolds 131 so that the hollow spaced 132 are lengthened in the longitudinal direction 10.

The scaffold structure 130 is cut out of a sheet having a predetermined length in the longitudinal direction 10 so that the transducers on the transducer patches 140 have the necessary transducer distribution. The width of the sheet, i.e. in the transverse sheet direction 20, is predetermined so that in can be attached around the catheter tube 110 without portions of the left side of the sheet overlaps portion of the right side of the sheet. In other words, as can be seen in FIG. 3, a continuous FPCB free surface portion 134 remains in the longitudinal direction 10. However, it is not necessary that the continuous FPCB free surface portion 134 comprises a straight line along the catheter 500. Here, patches 141 and 142 at the left and right sheet border, respectively "block" such a straight line. But it always exist—over the length of the structure—at least one, possibly meandering way of said FPCB free surface portion 134. In other words, every longitudinal line 10 at the circumference comprises portions of the FPCB free spaces 132 and/or free spaces from the FPCB free spaces 132 as well as portions of the straight scaffolds 131 and at some places transducer patches 140 as well as said FPCB free surface portion 134.

FIG. 11 shows a sequence of two-hexagon-wide FPCB free spaces 132. The width can also be only one or more than two hexagonal FPCB free spaces 132 depending on the internal angle alpha 36 and internal angle beta 35 shown in FIG. 1 and the size of the catheter tube 110.

FIG. 13 shows an electronic component 160 that is placed on the FPCB 120 and is thermobonded inside the catheter tube 110. The catheter opening 111 provides space for the electronic component 160 and electronic traces 161 are connecting the electronic component 160 with the FPCB connector on the distal end of the FPCB 120

FIG. 14 shows an electronic component 160 that is placed on the FPCB 120 and is thermobonded outside of the catheter tube 110. The catheter opening 111 provides space for the electronic component 160 and electronic traces 161 are connecting the electronic component 160 with the FPCB connector segment 139 on the proximal end of the FPCB 120.

FIG. 15 shows the example of a complete catheter 100 similar to the one shown in FIG. 4. Starting from the distal end there is a FPCB transducer segment 138 followed by a segment where electronic components 160 are placed. Extending from the FPCB transducer segment 138 there is a FPCB tail segment 136 that transitions in to the FPCB connector segment 139. The FPCB tail segment 136 can be folded in a 180 angle to extend the length in the longitudinal direction of the FPCB 120. This folding happens at the FPCB folding segment 137.

FIG. 16 shows a schematic drawing of a FPCB sheet 120 for an embodiment similar to FIG. 3. This FPCB sheet is used and shown in a perspective view of FIG. 17 wound around a catheter segment 110 creating a catheter 600; and finally FIG. 18 shows a perspective view of the catheter 600 of FIG. 17 with the surrounding FPCB sheet 120 bent in an exaggerated angle shown by arrow 171. In this context "exaggerated" means that introducing the catheter 600 in a vessel of a patient will not require such a bending angle, but it shows that even such bending angles are possible without damaging the FPCB print 120 and put transducers on the transducer patches 140 out of functioning.

FIG. 16 shows a FPCB sheet 120 with a sequence of hexagonal and diamond or ellipsoid shaped FPCB free spaces 132, wherein transducer patches 140 are provided at corners of the hexagonal shaped FPCB free spaces 132 as well as near the transition segments between diamond or ellipsoid and hexagonal shapes extending into a hexagonal shaped FPCB free space 132. It is possible, if two such transducer patches 140 are provided extending into the same hexagonal shaped FPCB free space 132 that they are connected with a FPCB web 165. The embodiment of FIG. 16 shows in schematical way two not interconnected streams 162 of adjacent traces 161 extending on opposite straight scaffolds 131 of hexagonal and diamond shaped FPCB free spaces 132 extending in the longitudinal direction of the FPCB sheet 120. In some parts only the most exterior and interior traces 161 are represented for the streams 162 of traces. FIG. 16 shows four or fives traces 161. This number, however, depends on the application case and can go up beyond ten traces 161.

Furthermore, only in the left part of FIG. 16 delamination preventing holes 150 are shown. These are a sequence of small holes in essentially constant distance one from another adjacent to any border of the FPCB sheet 120. They are at least provided around the inner FPCB free spaces 132 but are preferably also provided along the outer edges of the FPCB sheet 120 (not shown in FIG. 16). When the FPCB sheet 120 is laminated on a catheter tube, the material of the catheter tube is flowing into the delamination preventing holes 150 and fix additionally the edges of the FPCB sheet 120 with the underlying catheter tube material.

FIG. 17 shows the FPCB sheet 120 of FIG. 16 applied on a catheter tube 110 creating the catheter 600, wherein the FPCB transducer segment starts in the direction of the arrow with the numeral 138'. The FPCB free surface portion 134 is essentially behind the drawing plan and only the adjoining surfaces adjacent to the diamond shaped FPCB part are visible in FIG. 17. Traces 161 are not shown in FIG. 17 but some delamination preventing holes 150 are there for illustrative purposes.

Said catheter 600 of the embodiment of FIG. 17 is shown bent in FIG. 18 in an about 90 degree angle. Every even slight bending angle creates in a side view or cross section view on the bending angle a concave bending depression 170 on the inside of the angle (<180 degrees) which is of course far more pronounced at the sharp about 100 degree concave bending 171, whereas on the opposite side of the bending a convex embossing 175 can be seen. Bending always happen either at the FPCB free surface portions 134 or at the internal FPCB free space 132. Both FPCB free surface portions 132 or 134 allows bending while the remaining scaffold structure 131 and 133 remain essentially as in the non-bent condition and allow the transition of the stream 162 of traces 161 on them which is here schematically shown at the corner.

The invention claimed is:

1. A catheter comprising:
   a catheter tube,
   a flexible printed circuit board (FPCB) transducer segment, and
   a FPCB free surface portion,
   wherein the FPCB transducer segment has:
      a scaffold structure with a plurality of FPCB surrounded free spaces and
      a plurality of predetermined placed transducer patches,
   wherein the FPCB transducer segment covers essentially
      a catheter circumference for a length of the FPCB transducer segment with exception of said FPCB free surface portion, and
   wherein a leftmost portion of a left side of the FPCB transducer segment is positioned in a recess of a right side of the scaffold structure.

2. The catheter according to claim 1, wherein the FPCB free surface portion and the plurality of FPCB surrounded free spaces constitute from 10% to up to 95% of surface coverage of a lateral surface of the catheter tube providing the FPCB transducer segment.

3. The catheter according to claim 1, wherein the plurality of FPCB surrounded free spaces have a shape of a polygon with a plurality of FPCB corners and a plurality of FPCB edges.

4. The catheter according to claim 3, wherein a shape of the polygon is both axial-symmetric and non-axial-symmetric with a plurality of the plurality of FPCB edges and the plurality of FPCB corners constituting essentially the shape of the polygon.

5. The catheter according to claim 4, wherein the plurality of FPCB surrounded free spaces are arranged in transducer patch clusters along a longitudinal direction or a transverse circumferential line to form the scaffold structure.

6. The catheter according to claim 3, wherein the plurality of FPCB surrounded free spaces have the shape of an axial-symmetric hexagonal honeycomb with a predetermined size and orientation along a longitudinal direction and a transverse circumferential line.

7. The catheter according to claim 3, wherein the plurality of FPCB corners of the plurality of FPCB surrounded free spaces are supplemented with circular roundings that enlarge or diminish a total FPCB free surface in order to disseminate stress along the plurality of FPCB corners.

8. The catheter according to claim 3, wherein the plurality of FPCB edges of the plurality of FPCB surrounded free spaces are supplemented with ellipsoid or other shapes that enlarge or diminish a total FPCB free surface in order to disseminate stress along the plurality of FPCB edges.

9. The catheter according to claim 1, wherein at least one of the predetermined placed transducer patches is positioned on a crosspoint area of the scaffold structure.

10. The catheter according to claim 9, wherein transducers placed on the predetermined placed transducers patches are connected with one or more traces provided within a predetermined straight scaffold area of the scaffold structure and neighboring crossing crosspoint areas of the scaffold structure connecting the transducers with an end of the catheter.

11. The catheter according to claim 10, wherein, where more than one trace is provided in a given straight scaffold structure area, at least two traces of these traces are provided at opposite edges of the given straight scaffold structure area and any further trace is provided at an equal distance between said two edge positioned traces.

12. The catheter according to claim 1, wherein at least one of the predetermined placed transducer patches is positioned on a straight scaffold area of the scaffold structure.

13. The catheter according to claim 12, wherein transducers placed on the predetermined placed transducers patches are connected with one or more traces provided on at least one side of the adjacent predetermined straight scaffold area of the scaffold structure and neighboring crossing crosspoint areas of the scaffold structure connecting the transducers with the end of the catheter.

14. The catheter according to claim 1, wherein a plurality of the FPCB surrounded free spaces have an ellipsoid shape preventing, circumventing, and/or compensating a kinking behavior of the catheter tube.

15. The catheter according to claim 1, wherein at least one transducer patch comprises a sensor or an actuator.

16. A catheter comprising:
   a catheter tube,
   a flexible printed circuit board (FPCB) transducer segment, and
   a FPCB free surface portion, wherein the FPCB transducer segment has:

a scaffold structure with a plurality of FPCB sur-
rounded free spaces and a plurality of predetermined placed transducer patches, wherein the FPCB transducer segment covers essentially
a catheter circumference for a length of the FPCB
transducer segment with the exception of said FPCB
free surface portion, wherein the FPCB transducer
segment has an outer circumference of a parallelogram
in a way that the FPCB free surface portion is essen-
tially helix-shaped, while the parallelogram FPCB
transducer segment follows an essential helix shape
around the lateral surface of the catheter.

17. The catheter according to claim 16, wherein the
plurality of FPCB surrounded free spaces have a shape of a
polygon with a plurality of FPCB corners and a plurality of
FPCB edges, wherein the shape of the polygon is both
axial-symmetric and non-axial-symmetric with a plurality of
the plurality of FPCB edges and the plurality of FPCB
corners constituting essentially the shape of the polygon.

18. The catheter according to claim 17, wherein the
plurality of FPCB surrounded free spaces are arranged in transducer patch clusters along a longitudinal direction or a
transverse circumferential line to form the scaffold structure.

19. The catheter according to claim 16, wherein at least
one of the predetermined placed transducer patches is posi-
tioned on a crosspoint area of the scaffold structure, wherein
transducers placed on the predetermined placed transducers
patches are connected with one or more traces provided
within a predetermined straight scaffold area of the scaffold
structure, and neighboring crossing crosspoint areas of the
scaffold structure connecting the transducers with an end of
the catheter.

20. The catheter according to claim 16, wherein at least
one of the predetermined placed transducer patches is posi-
tioned on a straight scaffold area of the scaffold structure,
wherein transducers placed on the predetermined placed
transducers patches are connected with one or more traces
provided on at least one side of the adjacent predetermined
straight scaffold area of the scaffold structure and neighbor-
ing crossing crosspoint areas of the scaffold structure con-
necting the transducers with the end of the catheter.

* * * * *